United States Patent [19]

Suzuki et al.

[11] Patent Number: 4,761,936
[45] Date of Patent: Aug. 9, 1988

[54] SYSTEM FOR AUTOMATICALLY HANDLING ROLLER BOTTLES FOR CELL CULTIVATION

[75] Inventors: Akira Suzuki; Hideki Matsukura, both of Tokyo, Japan

[73] Assignee: Kirin Beer Kabushiki Kaisha, Tokyo, Japan

[21] Appl. No.: 99,341

[22] Filed: Sep. 21, 1987

[30] Foreign Application Priority Data

Sep. 24, 1986 [JP]  Japan ............................ 61-146054[U]

[51] Int. Cl.⁴ .............................................. B65B 31/02
[52] U.S. Cl. ........................................ 53/510; 53/167; 53/282; 53/425; 53/468
[58] Field of Search ................. 53/510, 167, 425, 426, 53/468, 282, 281, 283, 50; 141/234, 171, 85, 93, 100

[56] References Cited

U.S. PATENT DOCUMENTS

| | | | |
|---|---|---|---|
| 2,748,005 | 5/1956 | Baier | 53/425 X |
| 3,564,805 | 2/1971 | Mumford | 53/468 X |
| 3,714,760 | 2/1973 | Roberts et al. | 53/510 |
| 4,494,363 | 1/1985 | Rica et al. | 53/468 X |
| 4,627,221 | 12/1986 | Buchner | 53/425 |
| 4,658,566 | 4/1987 | Sanfilippo | 53/510 X |
| 4,717,575 | 1/1988 | Larroche | 53/425 X |

*Primary Examiner*—James F. Coan
*Attorney, Agent, or Firm*—Ladas & Parry

[57] ABSTRACT

Cells, particularly animal cells, are cultivated in roller bottles which are handled or processed by a system comprising a decapper, the first liquid sucking and filling machine in which culture medium is sucked and a bottle cleaning liquid is supplied, a bottle rolling mechanism for washing the inner wall of the bottle in a horizontally-reclined state while rolling the same, the second liquid sucking and filling machine in which the cleaning liquid is sucked and culture medium is supplied, and a capper. The decapper, the first liquid sucking and filling machine, the bottle rolling mechanism, the second liquid sucking and filling machine, and the capper are all located in an aseptic chamber in this order along a conveyor which extends between a bottle supply turn table and a bottle collecting turn table.

7 Claims, 4 Drawing Sheets

| | DECAP | SUCK 1 | FILL 1 | ROLL | SUCK 2 | FILL 2 | CAP |
|---|---|---|---|---|---|---|---|
| STEP 1 | ○ | → | ○ | → | → | ○ | ○ |
| STEP 2 | ○ | ○ | ○ | ○ | ○ | ○ | ○ |
| STEP 3 | ○ | → | → | → | ○ | ○ | ○ |
| STEP 4 | ○ | ○ | → | → | → | → | ○ |

SYSTEM FOR AUTOMATICALLY HANDLING ROLLER BOTTLES FOR CELL CULTIVATION

BACKGROUND OF THE INVENTION

This invention relates to a system for handling rotary cylinder type cell culturing containers (hereinafter called "roller bottles") particularly for animal cell culture, in which a series of processes such as filling of culture medium into the roller bottles, cell inoculation, and rinsing of the roller bottles are automatically performed.

Conventionally, in general, a hollow fiber, a microcarrier suspension culturing container, or the like is used as a culturing system for adhesive animal cells. However, there are some kinds of cells which can be cultured only in a roller bottle or small volume, and in the cultivation of the cells by using the roller bottle of this character, generally having an inner volume of about 500–1,000 ml, the culture medium filling process, the cell inoculation process, and the like process are manually performed.

Accordingly, when much volume of cells is to be cultured by using the roller bottles, much manual work or labour is required, which results in increasing in the contamination degree to the cells, and moreover, in the case where a DNA recombinant cell is processed, there is a fear of harming the body of the operator.

In order to eliminate the disadvantages or drawbacks described above, the full automated cultivating process under the aseptic condition with no operator, using a playback type robot, has been considered. With this operation, however, substantially the same numbers of robots as those of operators are required, and thus the whole system or equipment is enlarged and sophisticated. In addition, the control or handling of the robots is considerably troublesome.

SUMMARY OF THE INVENTION

An object of this invention is to eliminate the disadvantages or drawbacks of the prior art technique of this field and to provide a system for automatically handling roller bottles for cell cultivation having relatively simple construction and capable of being easily controlled without using playback type robots to undergo culture medium filling, cell inoculation into the roller bottles and the like processes under aseptic condition without manual work.

According to this invention, this and other objects can be achieved by providing a system for automatically handling roller bottles for cell cultivation comprising a starting station for supplying roller bottles to be processed, a terminal station for collecting the processed roller bottles, a conveyor operatively connected to the starting and terminal stations, an aseptic chamber disposed between both the stations, the conveyor extending throughout the aseptic chamber, a device located along the conveyor for opening a cap of the bottle (hereinafter called "decapper"), a first liquid sucking and filling machine located along the conveyor, a roller bottle rolling device located along the conveyor for rolling the roller bottle in a horizontally-reclined state, a second liquid sucking and filling machine located along the conveyor, and a device located therealong for closing the cap of the roller bottle (hereinafter called "capper"). Further the decapper, the first liquid sucking and filling machine, the roller bottle rolling mechanism, the second liquid sucking and filling machine, and the capper are all located in the aseptic chamber along the conveyor in this order.

In a preferred embodiment, the liquid sucking unit of the first liquid sucking and filling machine is equipped with a mechanism for tilting the roller bottle for substantially wholly sucking the liquid in the roller bottle, and the first and the second liquid sucking and filling machines are driven by positive displacement pumps.

According to the system having the construction described above, the cap of the roller bottle conveyed on the conveyor in the upright state in the aseptic chamber is opened by the decapper, and the culture medium in the roller bottle is then sucked by the first liquid sucking and filling machine. The roller bottle is thereafter rolled by the rolling mechanism in the horizontally-reclined state to wash the inner wall thereof with a cleaning liquid. The cleaning liquid is sucked by the sucking unit of the second liquid sucking and filling machine and then new culture medium is filled into the roller bottle. The roller bottle is thereafter closed by the capper and conveyed out of the aseptic chamber.

Further characteristics and advantages of this invention will become apparent from the detailed description of a particular embodiment, illustrated by way of non-limitative example in the accompanying drawings.

DESCRIPTION OF THE PREFERRED EMBODIMENTS

Figure 1:
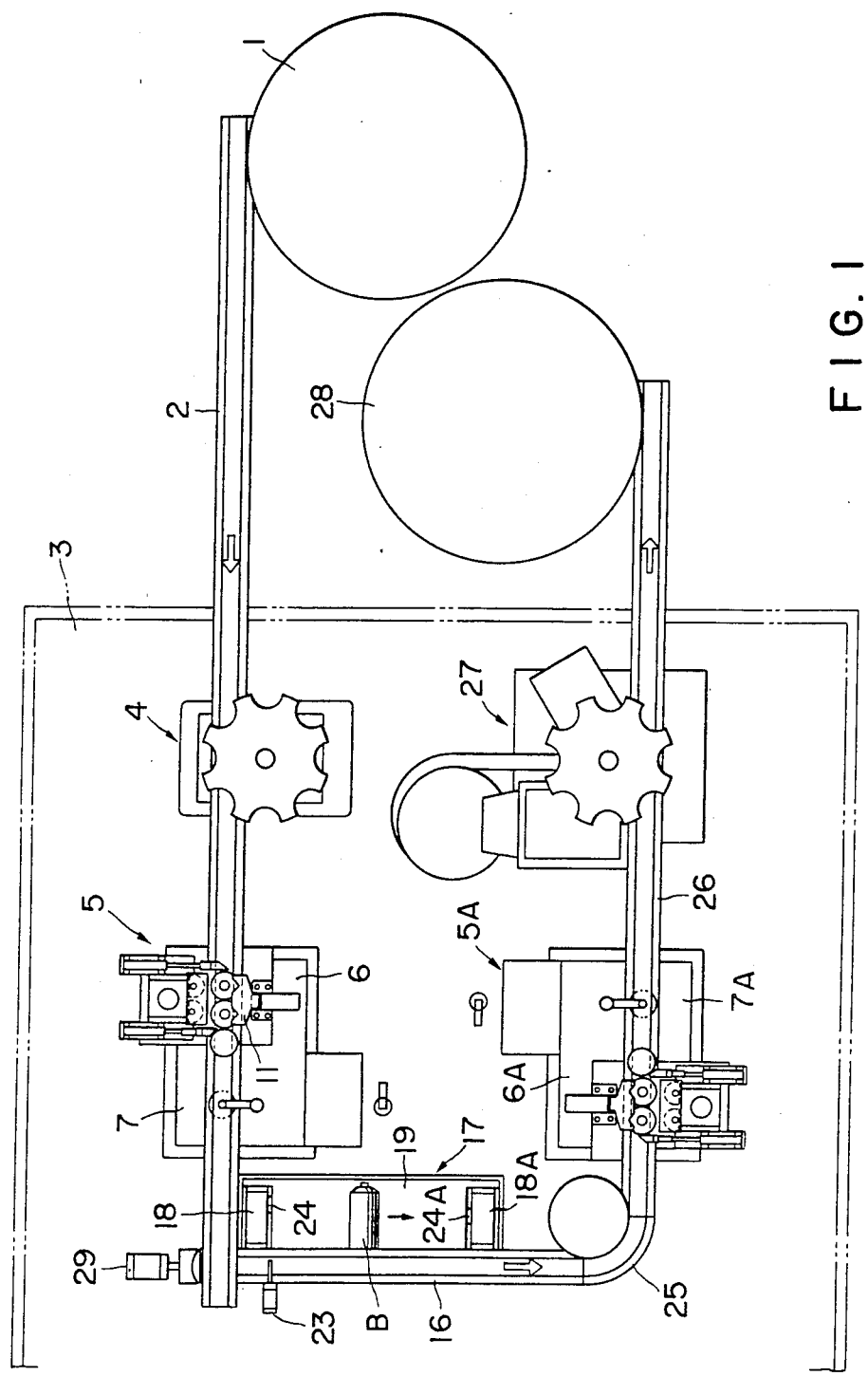
FIG. 1 is a schematic plan view of a system according to this invention.

FIG. 1 is a schematic plan view of a system for handling or processing roller bottles adapted to cultivate cells, in which reference numeral 1 designates a turn table as a starting station on which a plurality of roller bottles B, each having a generally cylindrical outer configuration, are put in all up-right state, and a conveyor 2 is arranged on the side of the turn table 1 so that the bottles B are transferred to the conveyor 2 from the turn table 1 in accordance with the rotation thereof. The conveyor 2 extends therefrom into an aseptic chamber 3 in which are disposed a decapper 4 for opening the caps of the bottles B and a first liquid sucking and filling machine 5 comprising a liquid sucking unit 6 and liquid filling unit 7. A positive displacement pump such as piston or cylinder assembly is utilized as a driving source of the first liquid sucking and filling machine 5. The liquid sucking unit 6 is equipped with a bottle tilting mechanism 8.

Figure 2:
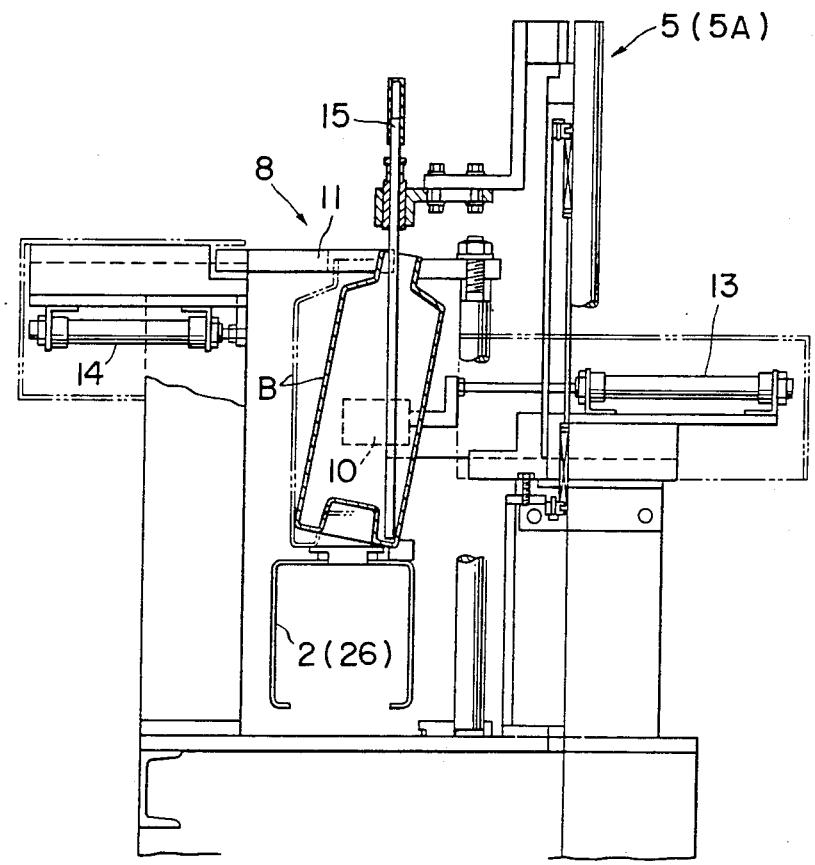
FIG. 2 is a side view, partially in section, of a liquid sucking and filling machine of the system shown in FIG. 1.
Figure 3:
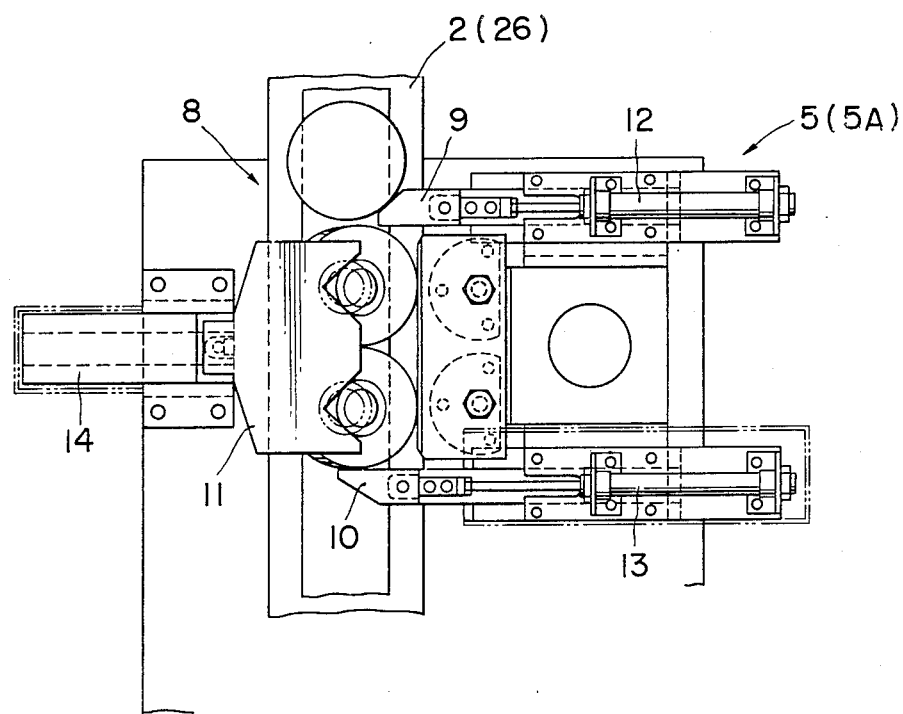
FIG. 3 is a plan view of the machine shown in FIG. 2.

The bottle tilting mechanism 8 comprises, as shown in FIGS. 2 and 3, front and rear stoppers 9 and 10 respectively disposed upstream and downstream sides along the conveyor 2 and a push plate 11 disposed on the side of the conveyor 2 between the front and rear stoppers 9 and 10. The stoppers 9 and 10 and the push plate 11 are constructed to be movable forwardly and rearwardly by the operations of cylinder assemblies 12, 13 and 14, respectively.

Under the condition wherein the front stopper 9 is retracted backwardly whereas the rear stopper 10 projects forwardly, the roller bottles B on the conveyor 2 advance therealong till the front side of the preceding roller bottle B abuts against the rear stopper 10 to thereby position the bottle B. After confirming the abutment, the front stopper 9 projects to stop the advancing of the following bottles B, and under these states, the roller bottle B located on the conveyor 2 between the front and rear stoppers 9 and 10 is inclined by pushing the push plate 11 forwardly from the conveyor 2. A vertically movable suction nozzle 15 of the first sucking unit 6 is inserted into the bottom portion of the inclined bottle B through the upper opening to suck the liquid filling therein, and after the sucking operation, the sucking nozzle 15 is drawn off and the push plate 11 is moved backwardly to return the bottle B to the upright position. The stopper 10 is then retracted and the bottle B after the liquid sucking operation is forwardly conveyed on the conveyor 2. The stopper 10 is thereafter caused to project forwardly and the front stopper 9 is retracted, and under these positional relationships, substantially the same procedures as described hereinbefore are repeated.

During the sucking operation, the liquid filling in the bottle B will be sucked with residual liquid of about 0.51 ml by sucking the liquid in the inclined bottle B.

In the illustrated embodiment, although two roller bottles B are simultaneously processed between the front and rear stoppers 9 and 10, it may be of course possible to process one or more bottles simultaneously.

Figures 4, 5:
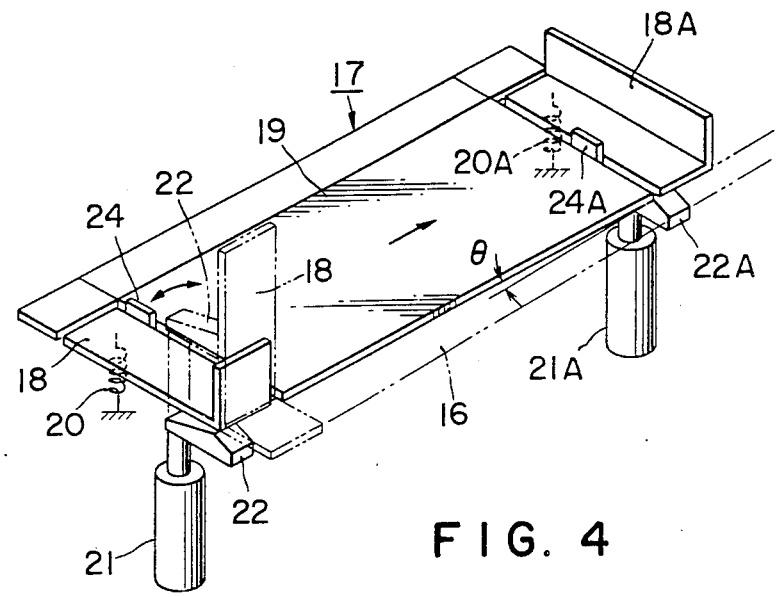
FIG. 4 is a perspective view of a roller bottle rolling device of the system shown in FIG. 1.
FIG. 5 is a table explanatory of roller bottle handling processes using the system shown in FIG. 1.

At the upstream end of the supply conveyor 2 is disposed a connection or coupling conveyor 16 so as to be operatively connected to the conveyor 2 in a perpendicular arrangement in a plane. A push cylinder assembly 29 is further located on the side of the conveyor 2 opposing the conveyor 16. As best shown in FIG. 4, in parallel to and alongside the conveyor 16 is arranged a device 17 which operates to bring down the roller bottle B, roll and raise the same, and hence the device 17 is called a roller bottle rolling device 17 hereinafter. The roller bottle rolling device 17 generally comprises a pair of recline and raise-up plates 18 and 18A disposed at both side ends of the device 17 for reclining and raising the roller bottle B, and an inclination plate 19 disposed between the recline and raise-up plates 18 and 18A. The inclination plates 19 inclines by angles θ from the front plate 18 towards the rear plate 18A so as to roll the roller bottle B on the inclination plate 19 by the self-gravity towards the advancing direction. Each of the recline and raise-up plates 18 and 18A is equipped with a spring 20 (20A) for downwardly urging the plate 18 (18A) to bring the same in the same plane as that of the location of the inclination plate 19, and a cylinder assembly 21 for raising the plate 18 (18A) against the urging force of the spring 20 (20A). A guide member 22 is further connected to the cylinder assembly 21 (21A). A retractable line stopper 23 is disposed along the conveyor 16 on the front side of the roller bottle rolling device 17 so as to oppose the recline and raise-up plate 18 of the front side. A stopper 24 is disposed on the outlet side of the front side plate 18 to be vertically movable, and substantially the same stopper 24A is also disposed on the inlet side of the rear side plate 18A.

The roller bottle B shifted from the conveyor 2 to the conveyor 16 is frowardly conveyed as it is by the operation of the push cylinder 29 when the line stopper 23 is retracted, whereas when it is required to roll the bottle B through the roller bottle rolling device 17, the line stopper 23 is made to project over the conveyor 16 and the front side recline and raise-up plate 18 is raised up by the actuation of the cylinder assembly 21. Under these conditions, when the roller bottle B is conveyed and stopped in abuttment against the line stopper 23, the plate 18 is reclined with the roller bottle B being also reclined by the reverse actuation of the cylinder assembly 21. The roller bottle B is then rolled on the inclination plate 19 towards the rear side plate 18A by downwardly moving the stopper 24. When the roller bottle B reaches the rear side plate 18A, the stopper 24 is again moved upwardly to prevent the next roller bottle B from being entered into the inclination plate 19, and the rear side plate 18A is then raised to displace the roller bottle B on the conveyor 16 by the actuation of the cylinder assembly 21A.

The rear end of the conveyor 16 is operatively connected through a guide plate 25 to another conveyor 26 extending in a direction normal to the conveyor 16 in a plane, i.e. substantially parallel to the conveyor 2. A second liquid sucking and filling machine 5A having substantailly the same structure as that of the machine 5 referred to hereinbefore and comprising a liquid sucking unit 6A and a liquid filling unit 7A is disposed along the conveyor 26 in the aseptic chamber 3. The second liquid sucking and filling machine 5A is driven by a positive displacement pump such as piston or cylinder assembly. The liquid sucking unit 6A is equipped with a bottle inclining mechanism 8A, which can hold the inclined bottle B, and under the condition, a vertically movable nozzle 15A of the liquid sucking unit 6A is inserted into the bottom of the inclined bottle B to suck the liquid therein.

A capper 27 for applying a cap to the opening of the roller bottle B is also located along the conveyor 26 at a forward portion of the second liquid sucking and filling machine 5A in the advancing direction of the bottle B. The conveyor 26 extends outward of the aseptic chamber 3 and the extended end portion of the conveyor 26 is operatively connected to a turn table 28 as a terminal station for collecting the processed roller bottles B.

A cultivating chamber, not shown, is located in the vicinity of the turn table 28 to accommodate the roller bottles B conveyed on the turn table 28, and the roller bottles B conveyed therein are placed respectively between two rollers under the reclined state. According to the rotation of the rollers, the bottles are also rotated, and during the rotation, the cultivating process is carried out for the predetermined time period.

The handling or processing system according to this invention having the construction described hereinabove is operated for the actual cell cultivation in accordance with the manner or processes described hereunder with reference to a table shown in FIG. 5.

In the first step, the roller bottle B transferred from the turn table 1 to the conveyor 2 is conveyed into the aseptic chamber 3 and the cap thereof is opened by the decapper 4 during its transportation on the conveyor 2, and when the bottle B reaches the first liquid sucking and filling machine 5, a first cultivating liquid is supplied into the bottle B by the liquid filling unit 7. The roller bottle B is then conveyed on and along the conveyors 2, 16 and 26, and a cell inoculation is made by the liquid filling unit 7A when the roller bottle B reaches the second liquid sucking and filling machine 5A located along the conveyor 26. The roller bottle B is thereafter closed by the capper 27 and conveyed and shifted on the collection turn table 28. A plurality of roller bottles thus collected on the turn table 28 are conveyed into the cultivation chamber, in which the bottles are rotated in the reclined state by the rollers thereby to cultivate the cells for the predetermined time period. The roller bottles B are then transferred on the turn table 1 with the upright state to perform the second step.

In the second step, the roller bottle B conveyed on the conveyor 2 is opened by the decapper 4, and the liquid contained in the bottle B is sucked by the liquid sucking unit 6 of the liquid sucking and filling machine 5, and a cleaning liquid is then supplied in the bottle B by the liquid filling unit 7. The bottle B is reclined by the front plate 18 and the inner wall thereof is washed and cleaned under the reclined state by the cleaning liquid during the rotation thereof when the bottle is rolled along the inclination plate 19 of the roller bottle rolling device 17. The bottle is raised by the rear plate 18A on the conveyor 16 and the cleaning liquid is sucked by the liquid sucking unit 6A of the second liquid sucking and filling machine 5A, and the bottle B is filled with a new culture medium (second culture liquid) by the liquid filling unit 7A. The bottle B is closed by the capper 27 and then conveyed on the collection turn table 28. A plurality of roller bottles B thus collected on the turn table 28 are transferred into the cultivating chamber for the cultivation for the predetermined time period in the manner as described with reference to the first step. After the predetermined time period, the roller bottles B are again conveyed on the turn table 1 for the third step.

Next, in the third step, the roller bottle B on the conveyor 2 opened by the decapper 4 is conveyed on and along the conveyors 2 and 16 as it is to the second liquid sucking and filling machine 5A, in which the liquid contained in the roller bottle B is sucked by the liquid sucking unit 6A and a new culture medium (third culture liquid) is supplied therein by the liquid filling unit 7A. After closing the cap the bottle B is transferred on the collection turn table 28 and the thus collected roller bottles are conveyed into the cultivation chamber in which the cultivation is performed for the predetermined period. The roller bottles B are again returned to the turn table 1 after the predetermined cultivation time period for the final fourth step.

In the fourth step, after the cap of the roller bottle B is opened, a paste as produced liquid is sucked and yielded by the operation of the liquid sucking unit 6 of the liquid sucking and filling machine 5. The roller bottle B passes as it is on the conveyor 16 and is closed when reaches the capper 27 disposed on the side of the conveyor 26. A series of steps thus finishes.

As is understood from the description regarding a series of cultivation processes, in the table of FIG. 4, circles mean the steps to be carried out and arrows represent the steps not to be performed in the respective processes.

As described hereinbefore, according to the system for handling roller bottles for cell cultivation, it can be precisely achieved to fill the culture medium into roller bottles, draw out the same, inoculate cells, and clean the inside of the bottle under aseptic condition without manual work. In addition, another specific device or machine such as playback type robots is not required, so that the entire structure of the system is relatively simple and can be easily controlled.

It is to be understood that the present invention is not limited by the embodiment shown in the drawings and described in the description which is given by way of example and that various changes or modifications may be possible without departing from the scope of the invention defined by the following claims.

What is claimed is:

1. A system for automatically handling roller bottles for cell cultivation comprising:
    a starting station for supplying roller bottles to be processed in an upright state;
    a terminal station for collecting processed roller bottles;
    an aseptic chamber disposed between said starting station and said terminal station;
    a conveyor means operatively connected to said starting and terminal stations so as to extend throughout an interior of said aseptic chamber;
    a decapper located along said conveyor means to open a cap of the roller bottle;
    a first means located along said conveyor means for sucking and filling liquid from and into the roller bottle;
    a rolling mechanism located along said conveyor means for rolling the roller bottle in a horizontally reclined state;
    a second means located along said conveyor means for sucking and filling liquid from and into the roller bottle; and
    a capper located along said conveyor means for closing the cap of the roller bottle;
    said decapper, said first liquid sucking and filling means, said rolling mechanism, said second liquid sucking and filling means, and said capper being all located in said aseptic chamber along said conveyor means in this order in a roller bottle conveying direction.

2. The system according to claim 1 wherein said starting station comprises a turn table operatively connected to a front end of said conveyor means and said terminal station comprises a turn table operatively connected to a rear end of said conveyor means.

3. The system according to claim 1 wherein each of said first and second liquid sucking and filling means is driven by a positive displacement pump.

4. The system according to claim 1 wherein each of said first and second liquid sucking and filling means comprises a unit provided with a nozzle means for sucking liquid from the roller bottle and a unit for filling liquid into the roller bottle.

5. The system according to claim 4 wherein said liquid sucking unit is equipped with a roller bottle inclining mechanism for sucking substantially entire liquid in the roller bottle.

6. The system according to claim 1 wherein said rolling mechanism comprises an inclination plate located in close contact with said conveyor means, front and rear recline and raise-up plates to be connected to front and rear ends of said inclination plate in operative association with said conveyor means, said inclination plate being downwardly inclined from said front raise-up and recline plate towards said rear raise-up and recline plate, means for operating said front and rear raise-up and recline plates to raise up or recline the same with the roller bottle, and means located along said conveyor means for stopping the advancing roller bottle on said conveyor means and putting the roller bottle on said front raise-up and recline plate.

7. The system according to claim 1 wherein said conveyor means comprises first, second, and third conveyors in a manner that said decapper and said first liquid sucking and filling means are located along said first conveyor, said roller bottle rolling mechanism is located along said second conveyor, and said second liquid sucking and filling means and said cap closing device are located along said third conveyor.

* * * * *